United States Patent [19]

Youngblood

[11] 4,387,165
[45] Jun. 7, 1983

[54] H₂S DETECTOR HAVING SEMICONDUCTOR AND NONCONTINUOUS INERT FILM DEPOSITED THEREON

[76] Inventor: James L. Youngblood, P.O. Box 58746, Houston, Tex. 77058

[21] Appl. No.: 370,790

[22] Filed: Apr. 22, 1982

[51] Int. Cl.³ .................... G01N 27/04; G01N 27/12; G01N 27/16
[52] U.S. Cl. ........................ 436/121; 73/23; 324/71.6; 422/90; 422/98
[58] Field of Search .................. 73/23; 324/71 SN; 422/90, 98; 436/121

[56] References Cited

U.S. PATENT DOCUMENTS

| | | | |
|---|---|---|---|
| 3,479,257 | 11/1969 | Shaver | 204/1 |
| 3,507,145 | 4/1970 | Loh | 73/23 |
| 3,567,383 | 3/1971 | Langley | 23/230 |
| 3,676,820 | 7/1972 | Taguchi | 338/34 |
| 3,695,848 | 10/1972 | Taguchi | 23/254 |
| 3,778,229 | 12/1973 | Webster | 23/254 |
| 3,793,605 | 2/1974 | Fehlner | 338/34 |
| 3,820,958 | 6/1974 | Cheng | 23/232 |
| 3,901,067 | 8/1975 | Boardman | 73/23 |
| 4,016,524 | 4/1977 | Pompei | 338/34 |
| 4,030,340 | 6/1977 | Chang | 73/23 |
| 4,169,369 | 10/1979 | Chang | 73/23 |
| 4,197,089 | 4/1980 | Willis | 324/71 SN |
| 4,223,550 | 9/1980 | Takahama | 73/23 |
| 4,224,280 | 9/1980 | Takahama | 422/98 |
| 4,277,439 | 7/1981 | Yasuda | 422/90 X |
| 4,324,761 | 4/1982 | Harris | 324/71 SN X |
| 4,338,281 | 7/1982 | Treitinger | 324/71 SN X |

FOREIGN PATENT DOCUMENTS 2636178  3/1977  Fed. Rep. of Germany.
56-1343  1/1981  Japan.

OTHER PUBLICATIONS

S. R. Morrison, "The Chemical Physics of Surfaces," Plenum Press, N.Y., 1977.

*Primary Examiner*—Sidney Marantz
*Attorney, Agent, or Firm*—Arnold, White & Durkee

[57] ABSTRACT

A method and apparatus for detecting hydrogen sulfide with improved longevity. The hydrogen sulfide detector includes a semiconductor comprised of indium oxide attached to an inert substrate. A noncontinuous film of an inert conductor such as gold is deposited on the semiconductor and means are provided for measuring a change in conductance of the semiconductor. In one embodiment tin oxide may be substituted for indium oxide. Also a method of detecting hydrogen sulfide including the steps of: coating a semiconductor with a noncontinuous film of an inert conductor, maintaining the temperature of the semiconductor in a range sufficient to insure proper response and recovery actions of the semiconductor when it is exposed to hydrogen sulfide; and exposing the coated semiconductor to a gas containing hydrogen sulfide while measuring the change in conductance in the semiconductor. The semiconductor may be made up of tin oxide or indium oxide and the inert semiconductor may be gold. The operational temperature for the semiconductor is preferably in the range of 150° to 300° C. In one embodiment the thickness of the semiconductor is at least 500 angstroms.

27 Claims, 6 Drawing Figures

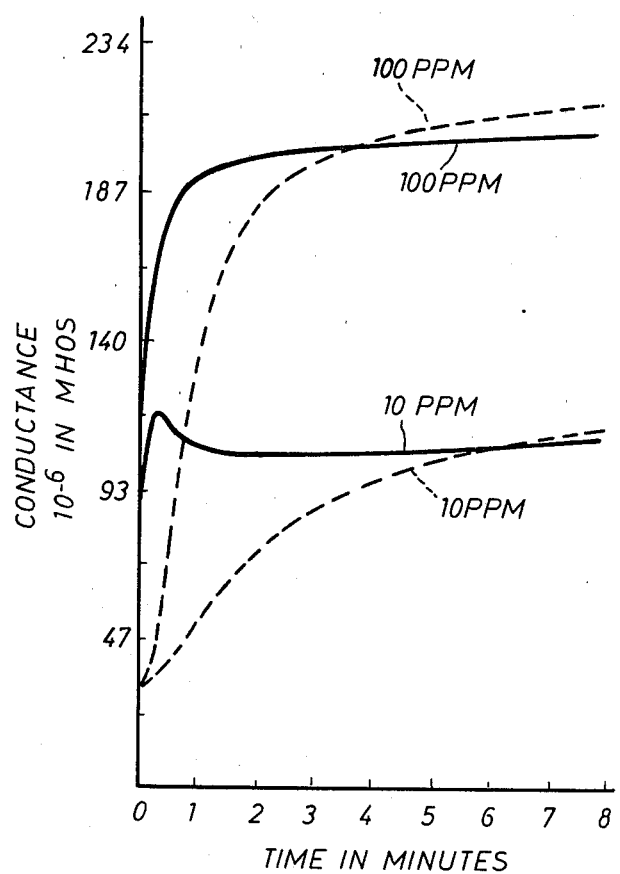

H₂S DETECTOR HAVING SEMICONDUCTOR AND NONCONTINUOUS INERT FILM DEPOSITED THEREON

BACKGROUND OF THE INVENTION

The invention relates to a method and apparatus of detecting gases and more particularly to a hydrogen sulfide detecting method and apparatus with increased longevity.

The need for reliable, inexpensive devices for detecting hydrogen sulfide and other gases has long been recognized. Sensors using semiconductors take advantage of the fact that certain substances adsorbed by a semiconductor influence the conductivity of a thin segment of film near the surface of the semiconductor. These devices generally comprise a metal oxide semiconductor mounted on an inert substrate. Dopants or impurities with a higher or lower valence are sometimes added to the metal oxide to affect conductivity. Additionally, catalysts are sometimes placed on the surface of the semiconductor to promote a reaction in the surrounding gas and so aid in detection.

A variety of these devices are disclosed in the patent literature. For example, Shaver, U.S. Pat. No. 3,479,257 discloses a hydrogen and reducing gas detector comprising a substrate made of quartz, alumina, or other substances, covered by a semiconductive thin film comprised of a metallic oxide. The metallic oxide is preferably an oxide of a metal selected from the group consisting of tungsten, molybdenum, chromium, niobium, nickel, iron, titanium, and the like. Thin film islands of a catalytic element are deposited upon the semiconductive film.

Boardman, U.S. Pat. No. 3,901,067 discloses a hydrogen sulfide detector with a semiconductor film of stannic oxide including indium as a possible dopant.

Chang, U.S. Pat. No. 4,030,340, employs a film of palladium deposited onto a semiconductor film in sensing hydrogen gas. An activation film which is preferably palladium, but also may be a palladium-gold alloy, is deposited as a myriad of discrete islands on a semiconductor film comprising stannic oxide with a dopant such as indium. The palladium or palladium-gold film acts as a catalyst to activate or dissociate diatomic hydrogen molecules.

Langley, U.S. Pat. No. 3,567,383 discloses a hydrogen detector with a thin film preferably of palladium oxide; while Fehlner, U.S. Pat. No. 3,793,605, discloses an ion sensitive device which employs a classical ferroelectric material to support a spray of gold islands.

These and other detectors suffer from one or more of several limitations. For example, many prior devices fail to provide sufficient longevity, while other devices are set to primarily detect hydrogen or gases other than hydrogen sulfide. Other devices rely on catalysts to break up the gases to be sensed. However, the catalysts are subject to poisoning, such that the sensor has a limited life. Still other devices are substantially detrimentally affected by humidity, while others require the pretreatment of the gas to remove hydrogen sulfide which slows response time. Still other devices are said to require repeated exposure to hydrogen sulfide if the device's efficacy as a sensor is to be maintained.

These and other limitations of prior processes and methods are substantially minimized, if not eliminated, by the present invention.

SUMMARY OF THE INVENTION

According to the present invention there is provided an improved method and apparatus for detecting hydrogen sulfide and other gaseous constituents which materially affect the conductance of a semiconductor. The hydrogen sulfide detector includes a semiconductor comprised of indium oxide attached to an inert substrate. A non-continuous film of an inert conductor such as gold is deposited on the semiconductor and means are provided for measuring a change in conductance of the semiconductor. In one embodiment tin oxide may be substituted for indium oxide. In another embodiment the semiconductor consists essentially of indium oxide or tin oxide.

The non-continuous film of the inert conductor may be made up of a series of islands with a significant horizontal linear dimension in the range of 10 to 1000 angstroms. In one embodiment the semiconductor may have a thickness of at least 500 angstroms.

A heating element may be provided to maintain the temperature of the semiconductor above the ambient temperature and hence speed the response and recovery actions of the detector. To this end a thin film heater may be adapted to maintain the temperature of the semiconductor at a substantially constant temperature in the range of 150° to 300° C. A temperature sensitive thin film, such as a thermistor, may also be included for controlling the temperature.

In still another embodiment there is provided an improved hydrogen sulfide detector including an inert substrate, a semiconductor mounted on the substrate, a continuous nonconductive film overcoating the semiconductor, a continuous conductive film overcoating the nonconductive film and means for measuring a change in conductance in the semiconductor. The semiconductor may be made up of indium oxide or tin oxide and the nonconductive overcoating may be selected from insulating oxides such as silicon oxide, aluminum oxide, or others known to those skilled in the art. The conducting film may be either selenium, tellurium, combinations thereof, or gold.

According to the present invention there is also provided a method of detecting hydrogen sulfide or other gaseous constituents which materially affect the conductance of a semiconductor including the steps of: coating a semiconductor with a noncontinuous film of an inert conductor; maintaining the temperature of the semiconductor in a range sufficient to insure proper response and recovery actions of the semiconductor when it is exposed to hydrogen sulfide; and exposing the coated semiconductor to a gas containing hydrogen sulfide while measuring the change in conductance in the semiconductor. The semiconductor may be made up of tin oxide or indium oxide and the inert conductor may be gold. The operational temperature for the semiconductor is preferably in the range of 150° to 300° C. In one embodiment the thickness of the semiconductor is at least 500 angstroms. Additionally, the conductance of the semiconductor may be calibrated with varying amounts of the hydrogen sulfide in a gas. This calibration may be conducted over a period of several months.

In accordance with the present invention there is also provided a method of detecting hydrogen sulfide including the steps of: depositing on an inert substrate a semiconductor comprising indium oxide; coating the semiconductor with a continuous thin film of a nonconductive material; coating the continuous thin film of nonconductive material with a conductive film; maintaining the temperature of the semiconductor film in a range sufficient to ensure proper response and recovery actions of the semiconductor when it is exposed to hydrogen sulfide; and exposing the coated semiconductor to a gas containing hydrogen sulfide while measuring the change in conductance in the semiconductor. Tin oxide may be substituted for indium oxide and the continuous conductive film may be either selenuim, telluruim, combinations thereof or gold.

BRIEF DESCRIPTION OF THE DRAWINGS

FIGS. 5 and 6 are graphs showing the response of various detectors with time.

Reference to these drawings will further explain the invention when taken in conjunction with the description of certain preferred embodiments.

DESCRIPTION OF THE PREFERRED EMBODIMENT

Figure 1:
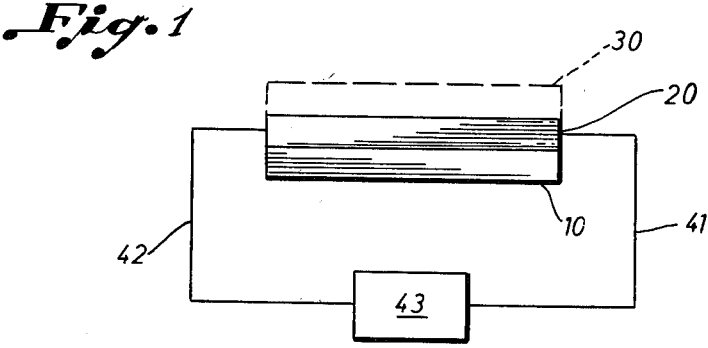
FIG. 1 is a schematic side view of a preferred embodiment of the present invention.
Figure 2:
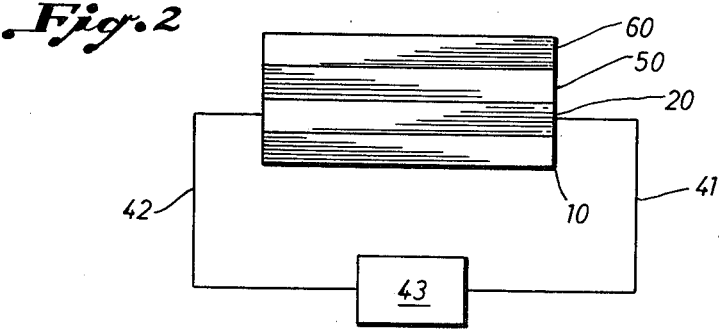
FIG. 2 is a schematic side view of another embodiment of the present invention.

Referring now to FIGS. 1 and 2, there will now be described an apparatus and process for detecting hydrogen sulfide in accordance with the present invention. Generally, the apparatus includes a substrate 10, a semiconductor film 20, a noncontinuous catalytically inert conductor 30 and means for measuring the change in conductance in the semiconductor film 20. The semiconductor film 20 may be made up of indium oxide or tin oxide while the noncontinuous inert conductor or coating 30 is preferably made of gold. The means for measuring the change in conductance of semiconductor film 20 may be made up of electrodes 41 and 42 attached to the semiconductor film 20 at one end and attached at the other end to a meter 43 which measures the change in electrical conductance of the semiconductor 20 between the electrodes.

The substrate 10 may be of any suitable inert material which has a negligible electrical conductivity and is stable at operating temperatures of the sensor. The substrate should also be such that the semiconductor film 20 will adhere to the substrate. The substrate may be an amorphous, polycrystalline or single crystal material and may comprise a single chip. Suitable materials include ceramics, quartz, alumina, sapphire, porcelain, zirconia, silicon oxide, or the like. Additionally, certain noninsulating materials such as silicon, can be used to support suitable materials such as silicon oxide.

The semiconductor film 20 is preferably comprised of indium oxide, but may also be comprised of tin oxide. The semiconductor film 20 may be deposited on the substrate 10 by a variety of processes, such as vacuum evaporation, known to those skilled in the art.

Given the limited depth to which the hydrogen sulfide molecules affect the conductivity of the semiconductor, the semiconductor film may be relatively thin. For example, it may be on the order of 200 to 300 angstroms. However, it preferably has a thickness of 500 to 1000 angstroms.

The magnitude of the change in conductivity increases as the thickness of the film decreases since a greater percentage of the atoms in the thinner film sense any elecelectrical changes on the surface. However, it is believed that the invention may also be practiced with thicker film semiconductors. Regardless of film thickness the change in electrical properties caused by the presence of the hydrogen sulfide can be detected as soon as the reaction takes place at the surface of the semiconductor due to the speed at which the electrons travel. By way of example, a film of 500 angstroms should respond to the sudden arrival of the hydrogen sulfide gas at the same rate as a film of 5000 angstroms, though the relative change in conductivity of the films will differ. Thus, it is believed that semiconductor layers with a thickness of 1000 to 10,000 angstroms or greater could be employed.

Unlike many prior processes, the use of dopants to increase the electrical conductivity of the semiconductor film is unnecessary. Thus, the semiconductor film preferably consists essentially of indium oxide or tin oxide. However, dopants or other impurities which do not substantially interfere with the response of the sensor to the hydrogen sulfide may be present.

The inert conductor 30 is deposited as a noncontinuous film on the surface of the semiconductor. In accordance with this embodiment of the present invention the covering of the catalytically inert conductor must be noncontinuous in order to avoid electrically shorting out the semiconductor. By way of example, a layer of gold may be deposited in the form of small nonconnected islands of approximately 100 to 500 angstroms in diameter or other significant horizontal linear dimension. Although the linear dimensions of the gold islands may be varied, for example, they may be up to 1000 angstroms in diameter, they should be of such a size that sufficient gaps remain to avoid electrically shorting out the semiconductor.

In accordance with the present invention the inert conductor 30 which covers the semiconductor film 20 is preferably not materially active as a catalyst. Catalysts are subject to poisoning and hence have reduced longevity.

Alternately, in accordance with another embodiment of the present invention as shown in FIG. 2 the semiconductor oxide film 20 may be first covered with a thin insulating film 50 followed by the deposition of a continuous film of an inert conductor 60. By way of example, the insulating overcoating or film 50 may be selected from such materials as silicon oxide, aluminum oxide or the like. The continuous conducting film, which must be deposited in such a way as to not electrically short out the semiconductor film, may be selected from the group consisting of selenium, tellurium, alloys of selenium and alloys of tellurium. Alternately, it may be gold.

The embodiment shown in FIG. 2 functions in much the same fashion as the one shown in FIG. 1. Meter 43 measures the change in conductance in semiconductor film 20 caused by the presence of hydrogen sulfide. The continuous nonconductive layer 50 should be thick enough to insulate and prevent shorting out of the semiconductor, but not so thick as to mask out the electrical effects caused by the presence of the hydrogen sulfide gas.

Figure 3:
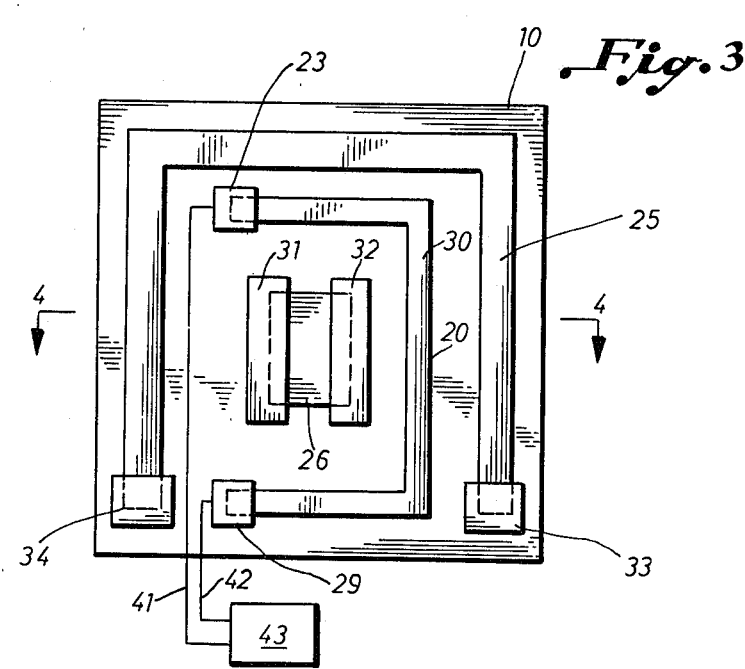
FIG. 3 is a schematic plan view of another preferred embodiment of the invention.

As the indium oxide or tin oxide semiconductors contain only a relatively small number of quasi-free electrons at room temperature, it is generally necessary to heat the semiconductor in the sensor. The temperature of the semiconductor is preferably maintained at or near a given temperature in the range of 150° to 300° C. Additionally, the approximate temperature at which the sensor is maintained should be relatively constant depending upon the desired accuracy of the responses to a given gas concentration. Thus, a heating element is preferably provided for maintaining the semiconductor film at a constant elevated temperature. For example, as shown in FIG. 3 a resistance heating element 25 may be placed on the substrate near the thin film semiconductor. The resistance heating element may be controlled by means of a temperature sensitive thin film, like thermistor 26, which may contact the substrate as shall be discussed in conjunction with FIGS. 3 and 4.

Any suitable resistance heating element and thermistor may be employed. By way of example, the resistance heating element may comprise a nickel chromium alloy, while the thermistor may comprise any one of a number of oxides known to those skilled in the art such as cobalt oxide, copper oxide, nickel oxide, iron oxide or combinations thereof. The thermister should be suitably protected from the atmosphere by means known to those skilled in the art.

Electrodes 41 and 42 may comprise either thin films deposited in contact with the semiconductor or metal strips or wires which are mechanically bonded to the semiconductor. The electrodes may be made of any suitable material which makes a good electrical contact with the indium oxide or tin oxide semiconductor film. By way of example, platinum, gold, or a platinum-gold alloy as well as copper, silver, chromium or nickel may be employed.

Resistors or other appropriate devices may be employed in lines 41 and 42. However, lines 41 and 42 as well as meter 43 are shown without regard to the particular circuitry used, since the details of the circuitry are known to those skilled in the art.

Figure 4:
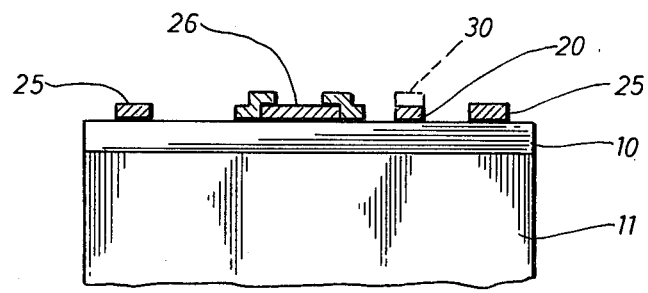
FIG. 4 is a schematic elevation of the embodiment shown in FIG. 3 taken off of line 4—4.

Another particular embodiment of a sensor in accordance with the present invention is depicted in FIGS. 3 and 4. A substrate 10 of silicon oxide is supported by a substrate of silicon 11. A nickel chromium resistance heating element 25 is mounted in U-shaped fashion on the silicon oxide substrate 10. Gold pads 33 and 34 serve to place the resistance heating element 25 in contact with an appropriate supply of electricity (not shown). As the silicon substrate 10 is a good thermal conductor, heat generated by nickel chromium heating element 25 is sufficient to maintain the indium oxide semiconductor film 20 at an appropriate temperature.

Indium oxide semiconductor film 20 is mounted in a C-shape fashion on silicon oxide substrate 10. As shown in FIG. 3 it is surrounded on three sides by the resistance heating element 25. The indium oxide semiconductor 20 is coated with a thin film of gold islands 30 as previously described. Gold pads 23 and 29 serve to place the thin film semiconductor 20 in contact with electrodes 41 and 42 and hence meter 43, which measures the change in conductivity in the indium oxide semiconductor.

Thermistor 26 is deposited on substrate 10 and gold pads 31 and 32 which are in turn deposited in electrical contact with the thermistor. Gold islands 31 and 32 serve to place the thermistor 26 in contact with an appropriate control system. As thermistor 26 is centrally mounted on substrate 10 surrounded on three sides by the thin film semiconductor 20 it is positioned to monitor temperature changes in the central portion of substrate 10 and hence indium oxide semiconductor 20.

As the temperature increases the resistance of the thermistor decreases. This change in resistance is in turn detected by the control system which is in electrical contact with the thermistor through gold islands 31 and 32. The control system in turn is electrically connected to the nickel chromium resistance heating element 25 and controls the amount of electricity supplied to the resistance heating element.

In calibrating the hydrogen sulfide sensing device a sensor such as one shown in FIGS. 3 and 4 is heated to an elevated operating temperature of about 150° to 300° C. in a hydrogen sulfide free atmosphere. By way of example, the sensor may be heated to a temperature of approximately 200° C. The electrical conductance across the film 20 is then measured by measuring the conductance across electrodes 41 and 42. Next, the sensor is placed in contact with a known concentration of hydrogen sulfide and the resultant change in conductance is measured. The process is then repeated for varying concentrations of hydrogen sulfide. The meter is subsequently set by methods known to those skilled in the art to measure changes in conductance greater than a certain threshold depending upon the concentrations of hydrogen sulfide which are to be detected.

In a similar fashion the conductance of the thin film semiconductor may be calibrated with varying concentrations of hydrogen sulfide for a given temperature, such that the meter readings may correspond to the concentrations of hydrogen sulfide in ways known to those skilled in the art. By way of example a given sensor might be exposed to varying quantities of hydrogen sulfide over periods of five to ten minutes each. In this regard it is noted that the response of the sensor may vary somewhat with longer periods of time. Consequently, any calibration of the device might take the variation of the response over time into account. Thus, it may be desired to conduct the calibration over a substantial period of time and provide for automatic adjustment of the system parameters to the varying response levels as time passes. For example, it may be preferable in some cases to take measurements over a period of several months, since in accordance with the present invention it is generally unnecessary to replace the sensor over substantial periods of time due to its increased longevity.

It has been said that hydrogen sulfide detectors must be repeatedly exposed to hydrogen sulfide to maintain a reasonable response. However, when calibrating a sensor operated in accordance with the present invention it is to be noted that when a sensor is away from hydrogen sulfide for a reasonable length of time—e.g. two weeks—the sensor will tend to have an initial faster response resulting in an over-shoot to hydrogen sulfide in concentrations of approximately 50 ppm or less. By way of example, as shown in FIG. 6, the response of the sensor is initially higher than its equilibrium response when exposed to air having a hydrogen sulfide concentration of approximately 10 ppm. This initial over response provides additional leeway in estimating threshold response in some cases.

It has been empirically determined that the sensor of the present invention also responds in a more limited degree to a variety of certain gases other than hydrogen sulfide. Hence a sensor in accordance with the present invention can be used to monitor and measure such atmospheric constituents as moisture, alcohol, hydrogen, volatile hydrocarbons and the like. However, as the response to these gases is less drastic than in the case of hydrogen sulfide, the detectors efficacy as a hydrogen sulfide detector with increased longevity should not be impaired. Moreover, it is believed that the protective effect of the gold islands or the continuous conductive film with a nonconductive layer of material will provide increased longevity for such sensors, and so increase the potential applications of the sensor of the present invention. By way of example, it is believed that a sensor constructed in accordance with the teachings of the present invention could be used as a "breathalyzer" to measure the alcohol content of air expelled from a person's lungs.

Examples will now be provided to further illustrate the present invention. Such examples are provided by way of illustration and are not intended to limit the scope of the invention.

EXAMPLE 1

An indium oxide semiconductor was deposited on a silicon-silicon oxide substrate and coated with a non-continuous conductive film of gold having an overall thickness of 62 to 83 angstroms. The overall arrangement of the sensor was similar to the embodiment shown in FIGS. 3 and 4.

The sensor was mounted using a silicon-gold eutectic as bonding agent, on a gold plated alloy cantilever connected to one of the pins of a header. Since the pins of the header were 0.5 inches (1.23 cm) high, the sensor was thermally insulated from the header. Gold wires were then connected between the gold pads on the sensor and the appropriate ends of the header pins using thermocompression bonding. With this arrangement it was found experimentally that in an ambient temperature of approximately 72° F. (22° C.) a power level of 0.30 watts was sufficient to maintain the sensor at 200° C. Using the relationships: $P=EI$, where $P$=power in watts, $E$=electrical potential in volts, and $I$=electrical current in amperes; and $E=IR$, where $R$=electrical resistance of the heater film in ohms; the correct voltage was determined to provide 0.30 watts to the sensor. For example, for a heater resistance of 333 ohms, the voltage required was 10.0 volts.

The indium oxide film with its overcoating of gold islands was connected electrically in series with a constant voltage source of 4.96 volts and a low-resistance resistor, usually with a resistance of 43.2 ohms±1%. A chart recorder was used to monitor the voltage across the low-resistance resistor. This monitored voltage was proportional to the conductance of the indium oxide film as shown in the equations below where $R_t$ is the resistance of the low resistance resistor and $R_s$ is the resistance of the indium oxide film:

$$I=E/R=4.96/(R_t+R_s)\approx 4.96/R_s,$$

since $R_s$ was generally an order of magnitude or more larger than $R_t$. Therefore, $$E_t=IR_t\approx(4.96/R_s)\times R_t=214/R_s.$$

Since $G_s=1/R_s$, where $G_s$=conductance of the indium oxide film, $$E_t=214\times G_s.$$

To evaluate the sensor response to hydrogen sulfide, the sensor was placed in a flow block attached with tubing to a permeation tube calibrator. The permeation tube was made of an appropriate plastic containing concentrated hydrogen sulfide gas. The gas was allowed to permeate through the tube walls at a rate which depends upon the temperature. Based on the rate of permeation of concentrated gas through the tube, the concentrated hydrogen sulfide was diluted with air flowing at a known controllable rate to produce the desired concentration of diluted hydrogen sulfide.

Figure 5:
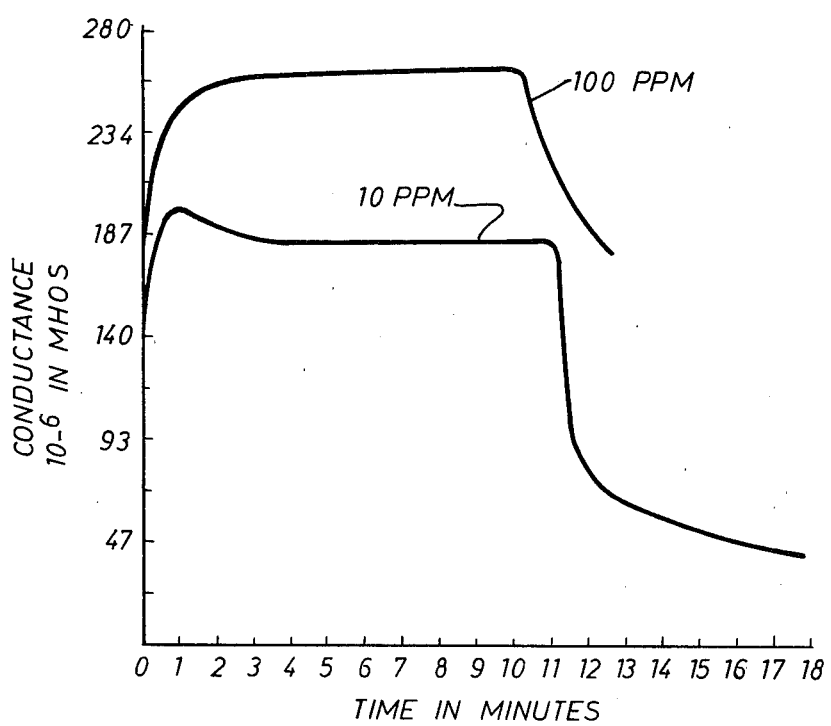

In a typical test the sensor would be allowed to stabilize in a flow of clean air of known humidity, then at time equal to zero the concentration of H$_2$S was suddenly changed from essentially zero to a fixed higher value such as 10, 50 or 100 ppm. This produced a time-varying response in the indium oxide film's conductance, which was being monitored by the chart recorder. Usually two such tests were conducted at two different H$_2$S concentrations. FIGS. 5 and 6 depict the type of graphs produced by the recorder.

After each evaluation the sensor was returned to a cage open to atmospheric air and was electrically heated at its operating voltage to produce a temperature of 200° C. where it was maintained continuously until the next evaluation.

The response of the sensor to hydrogen sulfide in known concentrations of 10, 50, and 100 parts per million was tested periodically over a period of several months. The results of those tests are shown generally in Table 1. The response time was chosen as time required for the rate of conductance change to slow to approximately 2% of its 50 ppm equilibrium conductance per minute.

TABLE 1

| Age of Sensor (Days) | Room Temp. | H$_2$S Concentration (ppm) | Response Time (Minutes) | Response Level (m mhos) |
|---|---|---|---|---|
| 1 | 40 | 10 | 3.5 | 0.46 |
|   | 40 | 100 | 2.2 | 0.64 |
| 13 | 73 | 10 | 1.8 | 0.26 |
|   | 73 | 100 | 1.8 | 0.43 |
| 26 | 70 | 10 | 1.1 | 0.16 |
|   | 70 | 100 | 2.5 | 0.30 |
| 65 | 74 | 10 | 4.0 | 0.15 |
|   | 74 | 100 | 2.8 | 0.26 |
| 92 | 76 | 10 | 1.1 | 0.19 |
|   | 76 | 100 | 2.0 | 0.26 |
| 240 | 74 | 50 | 1.2 | 0.19 |

As the data in Table 1 indicate, although there was some variation in response the rate of response remained quite fast. In fact when the sensor had not been exposed to hydrogen sulfide for several weeks there was a tendency for the sensor to slightly overshoot. As indicated by the last entry in Table 1 after eight months the sensor readily responded to a hydrogen sulfide concentration of 50 parts per million.

EXAMPLE 2

As a point of comparison longevity tests were conducted on indium oxide sensors which did not have an inert conductive overcoating. The tests were conducted in much the same fashion as those discussed in conjunction with Table 1.

As shown by the data in Table 2 the responses of the sensor were substantially slower than the gold coated sensors in Example 1. As with Table 1 the response time was chosen as the time required for the rate of conductance change to slow to approximately 2% of its 50 ppm equilibrium conductance per minute.

TABLE 2

| Sensor Number | Age of Sensor (days) | H2S Concentration (ppm) | Response Time (min) |
|---|---|---|---|
| 1 | 1 | 50 | 5.5 |
|   | 91 | 50 | 3.9 |
| 2 | 1 | 50 | 4.4 |
|   | 91 | 50 | 4.9 |
| 3 | 1 | 50 | 3.3 |
|   | 350 | 10 | 5.4 |
|   |   | 100 | 4.6 |

While not completely clear, it is believed that the portions of the indium oxide surface exposed to the hydrogen sulfide gas eventually become contaminated while the gold islands are practically immune to such contamination. Thus in the early weeks of the sensor's life change in conductivity brought on by the presence of hydrogen sulfide is the sum of a rapid change from response of both the protected and exposed segments of the indium oxide. As time passes this is followed by a gradually slowing change due to the diminishing response of the partially contaminated exposed indium oxide. Eventually the exposed segments of the indium oxide become so sluggish in their response to hydrogen sulfide that the response is dominated by the protected portions of the indium oxide. From this time on the response is due to the electrical conductivity of the indium oxide semiconductor resting under the gold islands. Thus, it is believed that the sensor goes through an unusual aging process in which it responds rapidly at first, sluggishly after one or two weeks and then rapidly again with no further substantial diminution of its response speed.

The response of a sensor in accordance with the present invention is further illustrated by the graphs shown in FIGS. 5 and 6. The graphs are based on the same type of data as used in Examples 1 and 2. The response is measured in millionths of a mho, while time is set forth in minutes.

FIG. 5 depicts the response of a semiconductor in accordance with the present invention some 92 days after the sensor was constructed. The sensor was exposed to 10 and 100 ppm of hydrogen sulfide gas, respectively as indicated in the Figures. The hydrogen sulfide fed to the detector was cut off at approximately 10 minutes for the 100 ppm concentration and at about 11 minutes for the 10 ppm concentration.

FIG. 6 graphically depicts the relative responses of a semiconductor as described in Example 1 (solid lines) as compared to the relative response of a semiconductor as described in Example 2 (dotted lines). Each sensor is approximately one year in age.

As can be seen in FIG. 6, the response of the sensor built in accordance with the present invention is significantly higher and faster, particularly during the first minute of exposure. Also shown in FIG. 6 is the tendency of the sensor to overshoot when exposed to lower concentrations of hydrogen sulfide.

Of course, further modifications and alternative embodiments of the apparatus and method of this invention will be apparent to those skilled in the art in view of the foregoing description. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes and modifications may be made which would be apparent to one skilled in the art after having the benefit of this description of the invention. It is intended that the following claims be interpreted to embrace all such modifications and changes as would be apparent to those skilled in the art.

What is claimed is:

1. A sensor for detecting gaseous constituents such as hydrogen sulfide which materially affect the conductance of a semiconductor comprising:
   an inert substrate;
   a semiconductor attached to the substrate and comprised of indium oxide;
   a noncontinuous film of an inert conductor deposited on the semiconductor; and
   means for measuring a change in conductance of the semiconductor.

2. A sensor for detecting gaseous constituents such as hydrogen sulfide which materially affect the conductance of a semiconductor comprising:
   an inert substrate;
   a semiconductor attached to the substrate and comprised of tin oxide;
   a noncontinuous film of an inert conductor deposited on the semiconductor; and
   means for measuring a change in conductance of the semiconductor.

3. The apparatus of claims 1 or 2 wherein the inert conductor is gold.

4. The apparatus of claims 1 or 2 wherein the noncontinuous film of the inert conductor comprises a series of islands with a significant horizontal linear dimension in the range of 10 to 1000 angstroms.

5. The apparatus of claims 1 or 2 further comprising a heating element.

6. The apparatus of claim 5 wherein the heating element is adapted to maintain the temperature of the semiconductor at a substantially constant temperature in the range of 150° to 300° C.

7. The apparatus of claim 5 further comprising a temperature sensitive thin film.

8. The apparatus of claim 7 wherein the temperature sensitive thin film is a thermistor.

9. The apparatus of claims 1 or 2 wherein the thickness of the semiconductor is at least 500 angstroms.

10. A hydrogen sulfide detector comprising:
    a inert substrate;
    a semiconductor deposited on the substrate, the semiconductor consisting essentially of indium oxide and having a thickness greater than 500 angstroms;
    a noncontinuous film of gold deposited on the semiconductor;
    electrodes connected to the semiconductor; and
    means attached to the electrodes for measuring a change in conductance of the semiconductor between the electrodes.

11. A hydrogen sulfide detector comprising:
    an inert substrate;
    a semiconductor mounted on the substrate and comprising indium oxide;
    a continuous nonconductive film overcoating the semiconductor;
    a continuous catalytically inert conductive film overcoating the nonconductive film; and
    means for measuring a change in conductivity in the semiconductor.

12. A hydrogen sulfide detector comprising:
    an inert substrate;

a semiconductor mounted on the substrate and comprising tin oxide;

a continuous nonconductive film overcoating the semiconductor;

a continuous catalytically inert conductive film overcoating the nonconductive film; and means for measuring a change in conductivity in the semiconductor.

13. The apparatus of claims 11 or 12 wherein the conductive overcoating is selected from the group consisting of selenium, tellurium, alloys of selenium, and alloys of tellurium.

14. The apparatus of claims 11 or 12 wherein the conductive overcoating comprises gold.

15. The apparatus of claims 11 or 12 wherein the combined depth of the continuous nonconductive film and the conductive film overcoating the nonconductive film is insufficient to materially mask out the effect of hydrogen sulfide on the semiconductor.

16. A method of detecting gaseous constituents such as hydrogen sulfide which materially affect the conductance of a semiconductor comprising the steps of:

coating a semiconductor comprising indium oxide with a noncontinuous film of an inert conductor;

maintaining the temperature of the semiconductor substantially constant at a temperature sufficient to ensure proper response and recovery actions of the semiconductor when the coated semiconductor is exposed to hydrogen sulfide; and exposing the coated semiconductor while the semiconductor is on an inert substrate to a gas containing hydrogen sulfide while measuring the change in conductance of the semiconductor.

17. A method of detecting gaseous constituents such as hydrogen sulfide which materially affect the conductance of a semiconductor comprising the steps of:

coating a semiconductor comprising tin oxide with a noncontinuous film of an inert conductor;

maintaining the temperature of the semiconductor substantially constant at a temperature sufficient to ensure proper response and recovery actions of the semiconductor when the coated semiconductor is exposed to hydrogen sulfide; and exposing the coated semiconductor while the semiconductor is on an inert substrate to a gas containing hydrogen sulfide while measuring the change in conductance of the semiconductor.

18. The method of claims 16 or 17 wherein the inert semiconductor is gold.

19. The method of claims 16 or 17 wherein the temperature of the semiconductor film is held substantially constant at a temperature in the range of 150° to 300° C.

20. The method of claims 16 or 17 wherein the thickness of the semiconductor is at least approximately 500 angstroms.

21. The method of claims 16 or 17 further comprising the step of calibrating the conductance of the semiconductor by exposing it to a gas with varying predetermined amounts of hydrogen sulfide in the gas.

22. The method of claim 21 wherein the calibration is conducted over a period of several months.

23. A method of detecting hydrogen sulfide comprising the steps of:

depositing a film of a semiconductor consisting essentially of indium oxide on an inert substrate;

depositing a noncontinuous film of gold on the semiconductor;

placing a heating element on the substrate;

using the heating element to maintain the temperature of the substrate in a range sufficient to ensure proper response and recovery actions of the semiconductor when it is exposed to hydrogen sulfide; and exposing the gold coated semiconductor film to hydrogen sulfide while measuring the change in conductance in the semiconductor film.

24. A method of detecting hydrogen sulfide comprising the steps of:

depositing a semiconductor comprising indium oxide on an inert substrate;

coating the semiconductor film with a continuous thin film of a nonconductive material;

coating the continuous thin film of nonconductive material with a conductive film;

maintaining the temperature of the semiconductor film in a range sufficient to ensure proper response and recovery actions of the coated semiconductor when it is exposed to hydrogen sulfide; and exposing the coated semiconductor film to a gas containing hydrogen sulfide while measuring the change in conductivity in the semiconductor film.

25. A method of detecting hydrogen sulfide comprising the steps of:

depositing a semiconductor comprising tin oxide on an inert substrate;

coating the semiconductor film with a continuous thin film of a nonconductive material;

coating the continuous thin film of nonconductive material with a conductive film;

maintaining the temperature of the semiconductor film in a range sufficient to ensure proper response and recovery actions of the coated semiconductor when it is exposed to hydrogen sulfide; and exposing the coated semiconductor film to a gas containing hydrogen sulfide while measuring the change in conductivity in the semiconductor film.

26. The method of claims 24 or 25 wherein the conductive film is selected from the group consisting of selenium, tellurium, alloys of selenium, and alloys of tellurium.

27. The method of claims 24 or 25 wherein the conductive material comprises gold.

* * * * *